Jan. 6, 1948. N. GRILLO Plant Pat. 778
ROSE PLANT
Filed July 16, 1946
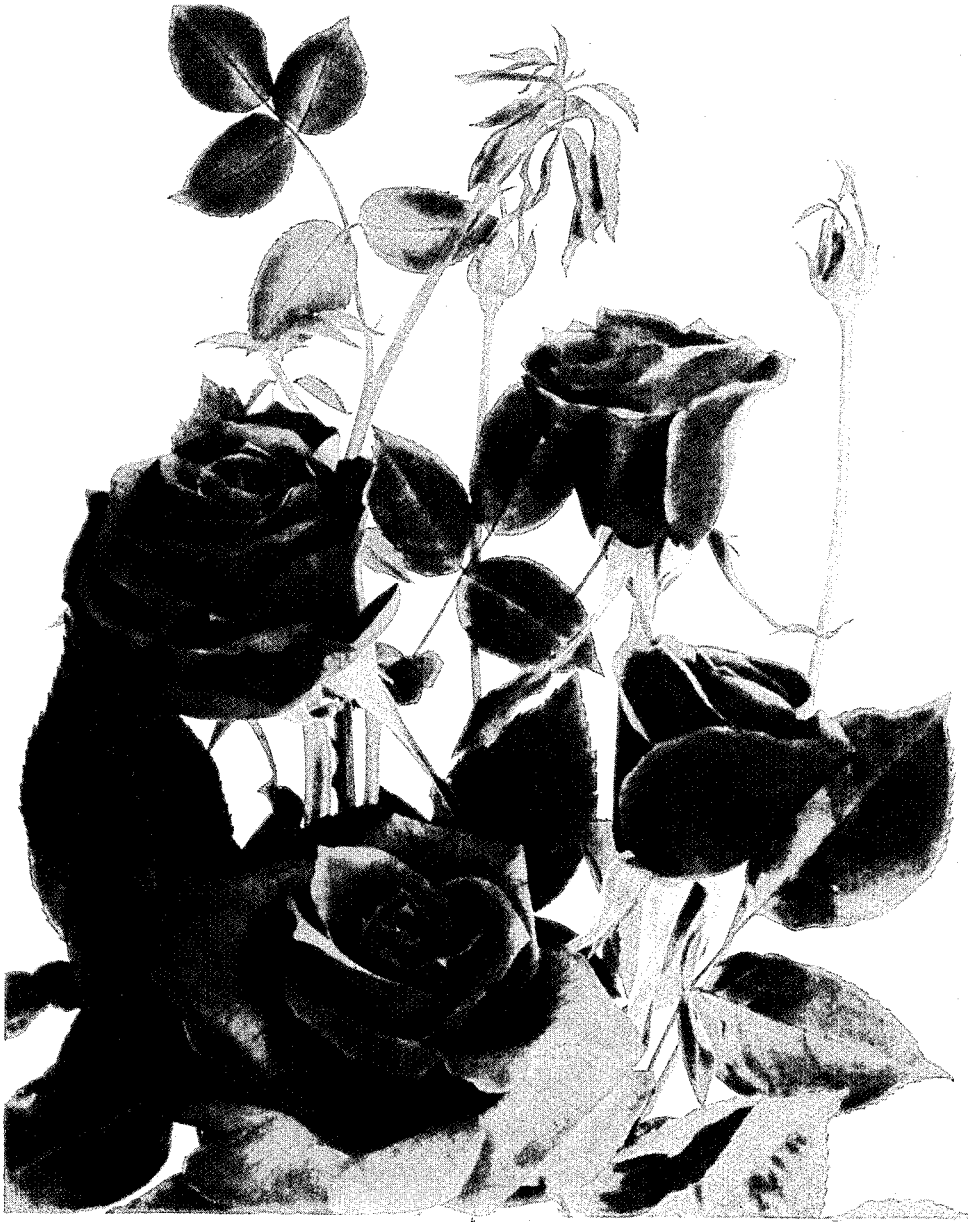
INVENTOR
Nicholas Grillo
By Orville M. Kile
Plant Pat. Agent Patented Jan. 6, 1948

Plant Pat. 778

UNITED STATES PATENT OFFICE

778

ROSE PLANT

Nicholas Grillo, Milldale, Conn.

Application July 16, 1946, Serial No. 683,839

1 Claim. (Cl. 47—61)

My present discovery relates to a new and distinct variety of hybrid tea rose plants. This variety was discovered by me as a sport of Regina Elena (Plant Patent No. 417.) It is much like its parent in form and growth of plant but its flower is of an entirely different color and it produces a great many more flowers in a season, the flowers having more petals with heavier substance.

The most outstanding feature of the new variety is the color and velvety aspect of the large flowers.

The variety has been asexually reproduced over a number of years and its characteristics have persisted.

Following is a detailed description of my new variety. Color plate references are to Ridgway's Color Standards and Nomenclature.

*The plant*

Growth:

*Habit.*—Very free-growing and vigorous.

*Form.*—Upright bush.

Blooming habit: Continuous. Very free and abundant bloomer.

Foliage:

*Leaflets.*—Three to five.

*Size.*—Medium. Terminal leaflet measures up to 3 inches by 1¾ inches.

*Shape.*—Oval with acuminate apex. Edges are sharply serrated.

*Color.*—Dark green, approximately Dark Cress Green (Plate XXXI).

*Quantity.*—Abundant.

*Stipules.*—Very small and narrow.

*Rachis.*—Short. Grooved and reddish-tinged above. Under side usually smooth.

Stems:

*Strength.*—Stout and strong although slender.

*Length.*—Medium to long.

*Internodes.*—Short and staggered.

*Thorns.*—A few small, greenish white thorns, downward pointing and irregularly spaced.

*The flower*

Bud:

*Shape.*—Pointed at first, becoming somewhat urn-shaped.

*Size.*—Short.

*Color.*—Dark velvet red, difficult to identify in Ridgway's but lying between Pomegranate Purple (Plate XII) and Carmine (Plate 1).

*Opening.*—Rather slow.

*Calyx.*—Sepals foliaceous. Reflex early.

*Peduncle.*—Lighter green than the stem, being approximately Lettuce Green (Plate V).

Bloom:

*Borne.*—Singly.

*Form.*—High centered at first. After several days all the petals reflex completely, making the flower pyramid-shaped.

*Size.*—Averages four or more inches across.

*Petalage.*—50 to 55 petals in the month of May.

*Color.*—When first open, between Tyrian Rose and Amaranth Purple (Plate XII), with a velvety sheen and brilliance. Just before shattering, the outer petals are between Rhodamine Purple and Aster Purple (Plate XII) on the upper surface and the inner petals are much lighter.

*Fragrance.*—Moderate.

*Lasting quality.*—Very good.

Petals:

*Size.*—Outer petals measure approximately 2½ inches each way.

*Shape.*—Almost round but with a pointed effect when reflexed.

*Substance.*—Heavy.

Reproductive organs:

*Pistils.*—Moderate number, set high on pithy knob. *Styles*—dull red. *Stigmas*—light yellow.

*Stamens.*—Few. Arise from base of pithy knob. Surround pistils. *Filaments*—light yellow and of uneven lengths. *Anthers*—small and dark yellow.

Having thus disclosed my discovery, I claim:

The new and distinct variety of hybrid tea rose plant, substantially as herein shown and described, characterized particularly by its free blooming habit and its large flowers of heavy substance, novel form, and distinctive dark red color with velvety sheen and brilliance.

NICHOLAS GRILLO.